(12) United States Patent
Joshi et al.

(10) Patent No.: US 6,283,461 B1
(45) Date of Patent: Sep. 4, 2001

(54) AUTOMATIC CYCLIC FLUID DELIVERY DEVICE AND ASSOCIATED PROCESS

(75) Inventors: Ashok V. Joshi; Truman Wold, both of Salt Lake City; John Joseph McEvoy, Sandy, all of UT (US)

(73) Assignee: Ceramatec, Inc., Salt Lake City, UT (US)

( * ) Notice: Subject to any disclaimer, the term of this patent is extended or adjusted under 35 U.S.C. 154(b) by 0 days.

(21) Appl. No.: 09/330,907

(22) Filed: Jun. 11, 1999

Related U.S. Application Data

(63) Continuation-in-part of application No. 09/028,372, filed on Feb. 24, 1998, now Pat. No. 6,109,539, which is a continuation-in-part of application No. 08/880,124, filed on Jun. 20, 1997, now abandoned.

(51) Int. Cl.$^7$ ........................................... B01F 3/04
(52) U.S. Cl. .................. 261/142; 261/35; 261/DIG. 65; 261/DIG. 88; 261/DIG. 89; 222/1; 222/61; 222/146.5; 222/494; 239/373; 239/533.13
(58) Field of Search .................. 261/30, 35, 142, 261/DIG. 17, DIG. 65, DIG. 88, DIG. 89; 222/1, 61, 146.5, 394, 400.5, 401, 420, 422, 490, 491, 494; 239/373, 533.13, 533.15

(56) References Cited

U.S. PATENT DOCUMENTS

| | | | |
|---|---|---|---|
| 1,007,026 | * 10/1911 | Forbes et al. | 261/DIG. 88 |
| 2,932,434 | * 4/1960 | Abplanalp | 222/394 |
| 3,431,393 | * 3/1969 | Katsuda | 261/DIG. 89 |
| 3,804,592 | 4/1974 | Garbe | 21/121 |
| 3,949,911 | 4/1976 | Morane | 222/386.5 |
| 4,173,604 | * 11/1979 | Dimacopoulos | 261/DIG. 88 |
| 4,513,884 | 4/1985 | Magid | 222/94 |
| 4,568,521 | * 2/1986 | Spector | 261/DIG. 89 |
| 4,595,564 | 6/1986 | Spector et al. | 422/125 |
| 4,635,857 | * 1/1987 | Hughes | 261/DIG. 65 |
| 4,759,501 | * 7/1988 | Silvenis et al. | 261/DIG. 88 |
| 4,785,972 | 11/1988 | LeFevre | 222/1 |
| 4,878,615 | * 11/1989 | Losi | 261/DIG. 88 |
| 4,923,095 | 5/1990 | Dorfman et al. | 222/386.5 |
| 4,953,763 | * 9/1990 | Kierum et al. | 222/422 |
| 5,000,383 | * 3/1991 | Van Der Heijden | 261/DIG. 88 |
| 5,171,485 | 12/1992 | Ryan | 261/27 |
| 5,234,140 | 8/1993 | Demarest et al. | 222/394 |
| 5,333,763 | 8/1994 | Lane et al. | 222/386.5 |
| 5,423,454 | 6/1995 | Lippman et al. | 222/1 |
| 5,549,247 | 8/1996 | Rossman et al. | 239/57 |
| 5,700,245 | 12/1997 | Sancoff et al. | 604/145 |
| 5,769,282 | 6/1998 | Lane et al. | 222/386.5 |
| 5,913,455 | * 6/1999 | La et al. | 222/146.5 |
| 6,109,539 | * 8/2000 | Joshi et al. | 239/43 |

\* cited by examiner

Primary Examiner—C. Scott Bushey
(74) Attorney, Agent, or Firm—Factor & Partners

(57) ABSTRACT

A fluid delivery device including a container for holding a predetermined quantity of fluid, a gas generator for generating gas within the container, and a dispenser for cyclically dispensing fluid at predetermined intervals out of the container without cyclical actuation by a user.

12 Claims, 3 Drawing Sheets

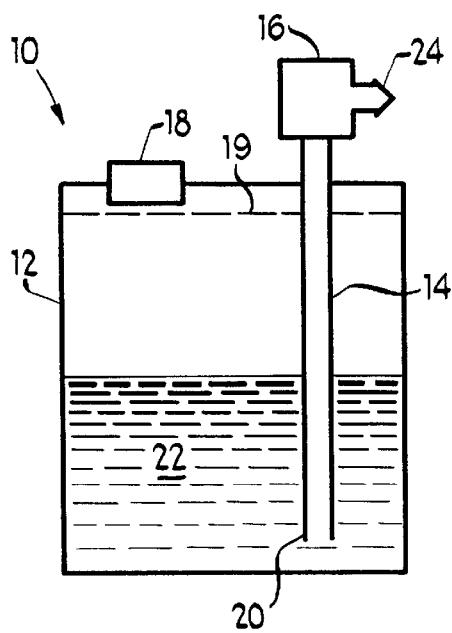
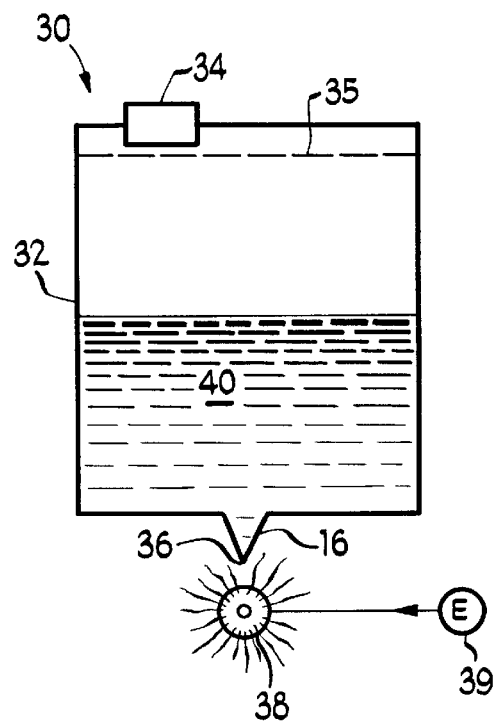
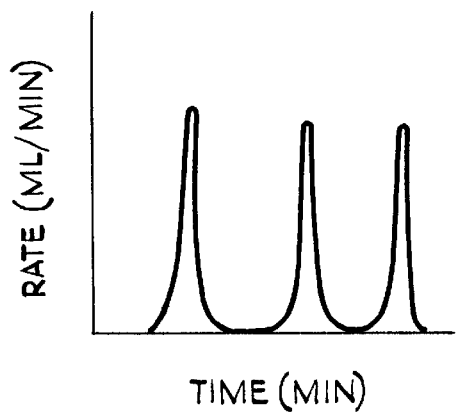
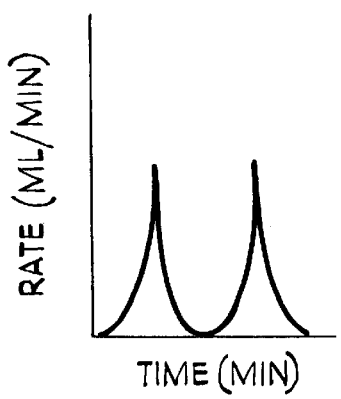

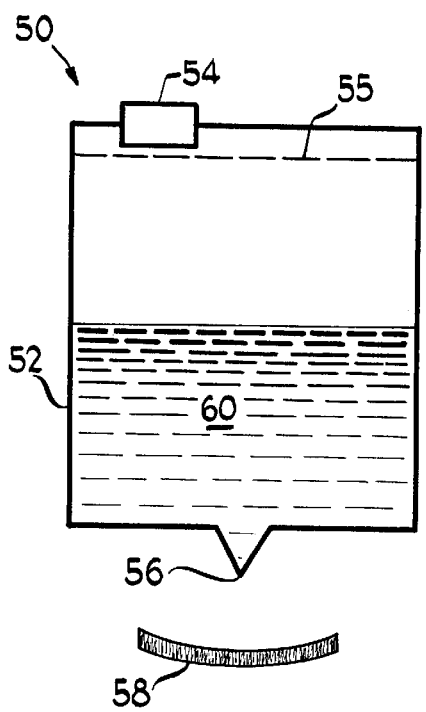
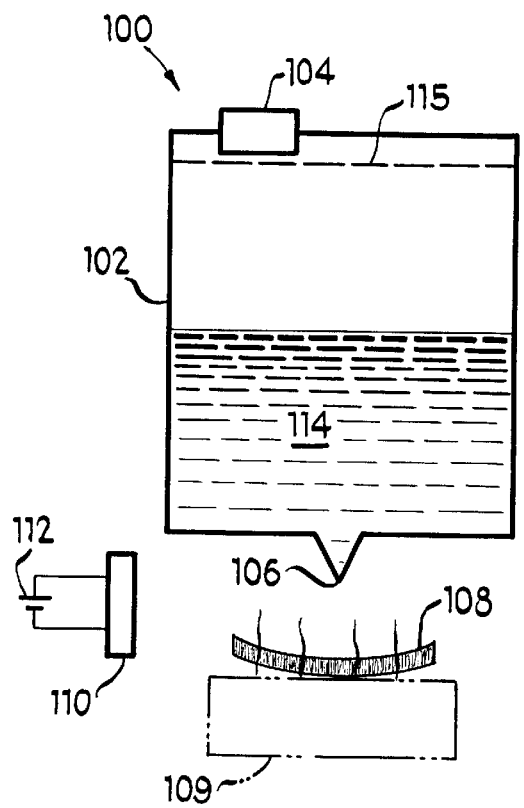
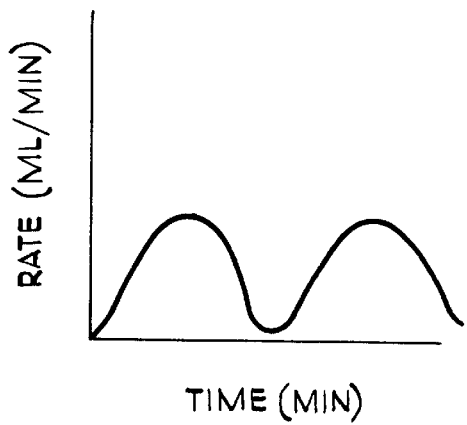
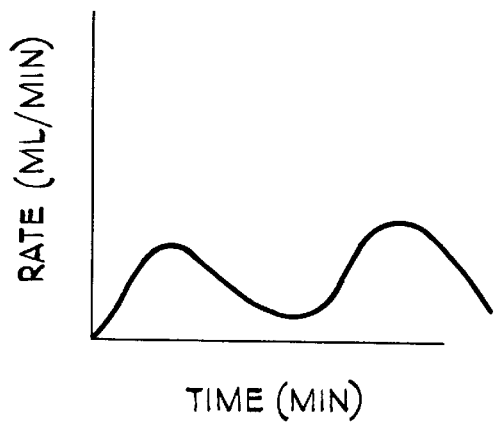

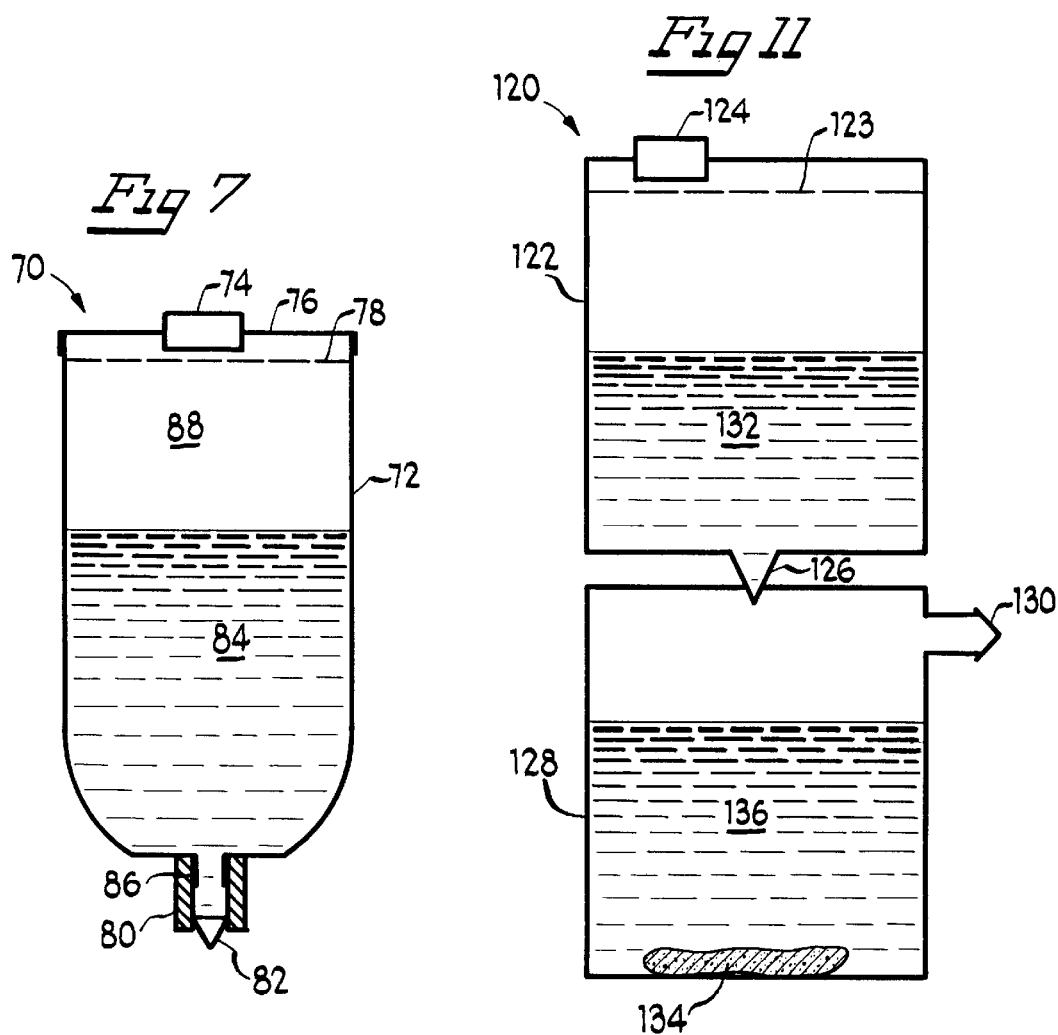
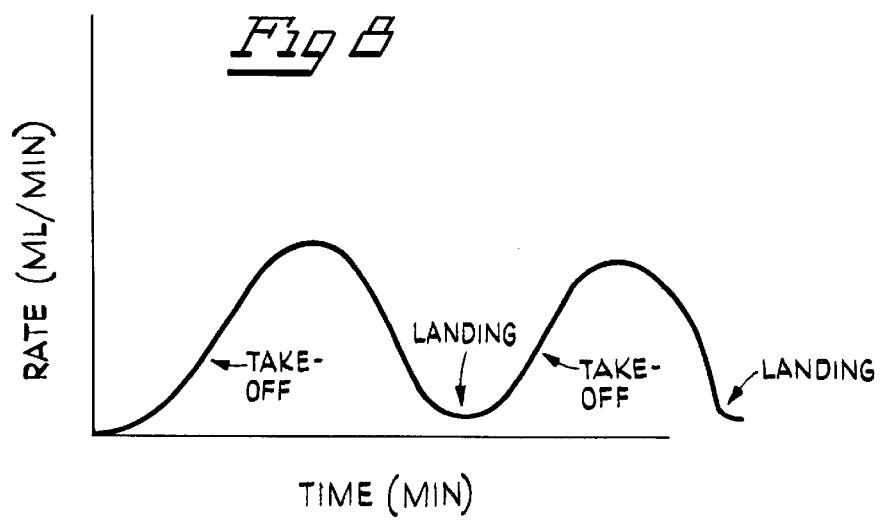

AUTOMATIC CYCLIC FLUID DELIVERY DEVICE AND ASSOCIATED PROCESS

CROSS-REFERENCE TO RELATED APPLICATION(S)

This application is a continuation-in-part of U.S. application Ser. No. 09/028,372, filed Feb. 24, 1998, now U.S. Pat. No. 6,109,539, which is a continuation-in-part of U.S. application Ser. No. 08/880,124, filed Jun. 20, 1997, now abandoned.

BACKGROUND OF THE INVENTION

1. Field of the Invention

The present invention relates in general to fluid delivery devices, and more particularly, to a fluid delivery device that is configured to automatically dispense fluid at predetermined intervals.

2. Background Art

Fluid delivery devices, such as fragrance or insect repellant dispensers have been known in the art for several years. While conventional dispensers have been readily utilized in numerous commercial markets, they have not been configured to automatically dispense a fluid at predetermined intervals. In particular, conventional dispensers are manually or electromechanically actuated by depressing, for example, a cap, a button, or a trigger mechanism. Such manually, or electromechanically actuated dispensers are cumbersome and expensive inasmuch as they have many costly components.

It is therefore an object of the present invention to provide a fluid delivery device that is configured to automatically dispense and/or volatize a fluid at predetermined intervals with mechanisms involving gas generating cells and materials, gravity force, heating elements, fans and combinations thereof.

These and other objects of the present invention will become apparent in light of the present Specification, Claims and Drawings.

SUMMARY OF THE INVENTION

The present invention is directed to a fluid delivery device comprising: a) a container for holding a predetermined quantity of fluid; b) means for generating gas within the container; c) means for cyclically dispensing fluid out of the container at predetermined intervals as well as optional means for vaporizing dispensed fluid.

In a preferred embodiment of the invention, the means for generating gas within the container comprises a gas generating cell. In this embodiment a shield may be used to substantially preclude fluid within the container from contacting the gas generating cell.

In another preferred embodiment of the invention, the means for cyclically dispensing and/or volatizing fluid at predetermined intervals comprises a one-way pressure relief valve. In this embodiment a stem may be used to direct fluid inside of the container toward the pressure relief valve.

In yet another preferred embodiment of the invention, the means for cyclically dispensing and/or fluid at predetermined intervals comprises an aperture associated with the container. Preferably the aperture is associated with a regulator to variably regulate the size of the aperture.

In a preferred embodiment of the invention, the device further comprises a heater for vaporizing the dispensed fluid. Preferably the heater is powered by a battery, a solar powered cell, or a supply of alternating current.

In another preferred embodiment of the invention, the device further comprises a fan for vaporizing the cyclically dispensed fluid. Preferably the fan is powered by a battery, solar cell or supply of alternating current.

In another preferred embodiment of the invention, the device further comprises an emanator pad associated with the container.

Preferably the device is at least partially filled with at least one of the group consisting essentially of perfume, fragrance, deodorizing fluid, insecticide fluid, sanitizing fluid, nutritional fluids, antimicrobial fluids, medication fluids or combinations thereof.

The present invention is also directed to a fluid delivery device comprising: a) a container for holding a predetermined quantity of fluid and b) means for cyclically dispensing and/or volatizing fluid at predetermined intervals out of the container.

In a preferred embodiment of the invention, the means for cyclically dispensing and/or cyclically volatizing the fluid at predetermined intervals out of the container comprises an aperture associated with the container. Preferably the aperture is associated with a regulator to variably regulate the size of the aperture.

The present invention is also directed to a fluid delivery device comprising: a) a container for holding a predetermined quantity of fluid, wherein the container includes at least one displacable flange; b) an elastomeric band seal associated with the at least one displacable flange; c) and an aperture covered by the elastomeric band seal.

The present invention is further directed to a fluid delivery devise comprising: a) a first container for holding a predetermined quantity of a first fluid, such as water; b) means for generating gas within the first container; c) a second container holding a predetermined quantity of a second fluid and a gas generating material that is activated by the first fluid; d) means for cyclically dispensing the first fluid out of the first container and into the second container; and e) means for cyclically dispensing the second fluid from the second container.

BRIEF DESCRIPTION OF THE DRAWINGS

The invention will now be described with reference to the drawings wherein:

FIG. 1 of the drawings is a schematic representation of a first embodiment of a fluid delivery device fabricated in accordance with the present invention;

FIG. 2 of the drawings is a schematic plot of fluid dispensing rate versus time for the fluid delivery device of FIG. 1;

FIG. 3 of the drawings is a schematic representation of a second embodiment of a fluid delivery device fabricated in accordance with the present invention;

FIG. 4 of the drawings is a schematic plot of fluid dispensing rate and/or volatizing rate versus time for the fluid delivery device of FIG. 3;

FIG. 5 of the drawings is a schematic representation of a third embodiment of a fluid delivery device fabricated in accordance with the present invention;

FIG. 6 of the drawings is a schematic plot of fluid volatizing rate versus time for the fluid delivery device of FIG. 5;

FIG. 7 of the drawings is a schematic representation of a fourth embodiment of a fluid delivery device fabricated in accordance with the present invention;

FIG. 8 of the drawings is a schematic plot of fluid dispensing rate versus time for the fluid delivery device of FIG. 7;

FIG. 9 of the drawings is a schematic representation of a fifth embodiment of a fluid delivery device fabricated in accordance with the present invention;

FIG. 10 of the drawings is a schematic plot of fluid dispensing rate versus time for the fluid delivery device of FIG. 9; and FIG. 11 of the drawings is a schematic representation of a sixth embodiment of a fluid delivery device fabricated in accordance with the present invention.

DETAILED DESCRIPTION OF THE DRAWINGS

While this invention is susceptible of embodiment in many different forms, there is shown in the drawings and will herein be described in detail several specific embodiments with the understanding that the present disclosure is to be considered as an exemplification of the principles of the invention and is not intended to limit the invention to the embodiments illustrated.

Referring now to the drawings and to FIG. 1 in particular, fluid delivery device 10 is shown as comprising container 12, stem 14, pressure relief valve 16, and gas generating cell 18. For purposes of the present invention, container 12 can be fabricated from numerous conventional materials including steel, various metallic alloys, and synthetic polymeric compounds such as, BAREX, high density polyethelene, polyvinyl chloride, high-density polyurethane and high-density polytetrafluoroethylene. It will be understood of course, that the precise fabrication materials used will depend upon the particular qualities desired, such as, for example, permeability, price, weight, strength, durability, corrosion resistance or any combination thereof. The only limitation relative to the fabrication materials of container 12 is that the container must be sufficiently strong and/or elastic enough to withstand the pressure generated from cell 18 without cracking or otherwise degrading.

Stem 14 is preferably a hollow piece of rigid or flexible plastic or metal having a generally circular cross section. It will be understood that stem 14 can be configured with any one of a number of geometric configurations as long as stem 14 includes a portion that is compatibly configured with pressure relief valve 16. Stem 14 is preferably positioned inside of container 12 and includes first end 20 that generally emanates towards the bottom of container 12 so that it can intake fluid 22 whether container 12 is generally empty or full. A second end of stem 14 is preferably frictionally mated to pressure relief valve 16. Of course, other securing mechanisms that would be known to those having ordinary skill in the art are likewise contemplated for use.

Pressure relief valve 16 comprises a conventional one-way valve. Pressure relief valve 16 can be fitted with any one of a number of nibs 24 ranging from a narrow angled needle point nib to a wide angled fan type nib—depending upon the particular application. In addition, pressure relief valve 16 can be configured to release pressure within fluid delivery device 10 at numerous pressures depending upon the internal configuration of the valve.

For purposes of the present invention, gas generating cell 18 can comprise any conventionally known device, as would be readily understood to those having ordinary skill in the electrochemical and/or chemical gas generating arts. Gas generating cell 18 can be associated with shield 19, which can be fabricated from, for example, polypropylene that is air permeable, yet substantially moisture impermeable. The shield protects cell 18 against contamination from, or splashing by, the fluid in the container.

In operation, gas generating cell 18 is activated by a button or switch (not shown). Once activated, gas generating cell 18 continuously generates gas inside of container 12, thereby building up pressure inside the container. Once a threshold pressure is reached, as determined by the internal set up of valve 16, the valve opens and an amount of fluid 22 runs up stem 14 and sprays out of nib 24, thereby lowering the pressure inside of container 12. After the pressure inside the container has been lowered, valve 16 shuts and the pressure begins to rebuild once again. This process is cyclical, requires no mechanical manipulation beyond initially activating cell 18, and can run until either the cell is deactivated or expires, or until the fluid in the container has been completely expelled.

As shown in FIG. 2, the schematic plot of delivery rate versus time for fluid delivery device 10 exhibits relatively sharp peaks, which are indicative of a burst like delivery.

Turning now to FIG. 3, a second embodiment of fluid delivery device 30 is shown as comprising container 32, gas generating cell 34, aperture 36, and heater 38. It will be understood that container 32 and gas generating cell 34 are configured similar to container 12 and cell 18 of fluid dispensing device 10. For purposes of the present disclosure, aperture 36 is preferably positioned near the bottom of container 32 so that gravity may be used to assist gas generating cell 34 in dispensing fluid 40 from device 30. Although not shown, aperture 36 can be configured with a regulator such as a pin, a screw, or a cap to alter the size of the aperture, and, in turn, the rate at which fluid is dispensed from the container.

Heater 38 is preferably fabricated from apiece of conductive metal, which is connected to an energy source 39, such as, for example, a battery, a solar cell or an electrical outlet.

In operation, gas generating cell 34 is activated by a button or switch (not shown), and can be optionally associated with a shield 35—similar to shield 19 of FIG. 1. Once activated, gas generating cell 34 continuously generates gas inside container 32, thereby building up pressure inside the container. With the assistance of gravity, the internal pressure forces fluid 40 inside of container 32 toward and into contact with one way valve 16. When the pressure upon the one way valve is great enough (based upon the particular valve), the valve will open and allow fluid 40 to be forced out through aperture 36 at a controlled rate. Once fluid 40 exits container 32, it contacts heater 38, which is powered by an electrical source, and readily evaporates or vaporizes into the atmosphere. After fluid 40 evaporates, additional fluid contacts the heater.

As the fluid is released out of the container, the pressure generated within the container begins to decrease. Accordingly, the one way valve will close when the pressure drops below the particular threshold necessary to keep the particular valve opened. Once the valve re-closes, pressure within the container continues to build until it again forces the valve to open, thereby creating a cyclical dispensing pattern. This cyclical process requires no mechanical manipulation beyond initially activating cell 34, and can run until either the cell is deactivated or expires, or until all of the fluid is expelled from the container.

Although not shown, it will be understood that fluid delivery device 30 can be configured to operate without gas generating cell 34. In this configuration, cell 34 is replaced with a sealable aperture and the force of gravity is solely responsible for dispensing the fluid onto heater 38. In such an embodiment, the size and construction of the aperture can be used to control the cyclic release of fluid.

As shown in FIG. 4, fluid delivery device 30 may have cyclic fluid delivery characteristics at predetermined intervals depending on, among other things, the rate of gas generation of cell 34, the volume of container 32, the viscosity of fluid 40, the size of aperture 36, and the surface area and temperature of heater 38.

Turning now to FIG. 5, a third embodiment of fluid delivery device 50 is shown as comprising container 52, gas generating cell 54, aperture 56, and emanator pad 58. It will be understood that container 52 is preferably configured similar to container 32 of fluid dispensing device 30. It will be further understood that gas generating cell 54 is preferably configured similar to cell 34 of device 30.

For purposes of the present disclosure, aperture 56 is preferably positioned near the bottom of container 52 so that gravity may be used to assist gas generating cell 54 in dispensing fluid 60 from device 50. Although not shown, aperture 56 can be configured with a regulator such as a pin, a screw, or a cap to alter the size of the aperture. Emanator pad 58 is ideally positioned below the container and is preferably fabricated from, for example, polyurethane foam or nylon. It is also contemplated that the emanator be in direct contact with the aperture. It will likewise be understood that the emanator pad can be fabricated from any one of number of materials, so long as the material is substantially compatible with the fluid it temporarily retains.

In operation, gas generating cell 54 is activated by a button or switch not shown, and can optionally be associated with shield 55—similar to shield 19 of FIG. 1. Once activated, gas generating cell 54 continuously generates gas inside container 52, thereby building up pressure inside of the container. With the assistance of gravity, the internal pressure forces fluid 60 inside of container 52 to exit through aperture 56 at a controlled rate. Once fluid 60 has exited container 52 it will deposit onto emanator pad 58. After fluid 60 is deposited onto emanator pad 58, it evaporates into the atmosphere at a rate which is primarily dependant upon the temperature and pressure of the container's surroundings. Once fluid 60 has evaporated, additional fluid will automatically be deposited onto the emanator pad. This cyclical process requires no mechanical manipulation beyond initially activating cell 54 and can run until either the cell is deactivated or expires, or the fluid in completely expelled from the container.

Although not shown, it will be understood that fluid delivery device 50 can be configured to operate without gas generating cell 54. In this configuration, cell 54 is replaced with a sealable aperture and gravity is solely responsible for dispensing the fluid onto the emanator pad 58.

As shown in FIG. 6, the schematic plot of delivery rate versus time for fluid delivery device 50 exhibits relatively broad peaks indicative of a more continuous delivery into the atmosphere. The breadth of the peaks will depend upon, among other things, the rate of gas generation of cell 54, the volume of container 52, the viscosity of fluid 60, the size of aperture 56, and, as previously mentioned, the temperature and pressure of the atmosphere surrounding the fluid delivery device. Turning now to FIG. 7, fluid delivery device 70 is shown as comprising container 72, gas generating cell 74, cap 76, shield 78, elastomeric band seal 80, and nib 82. It will be understood that container 72 and gas generating cell 74 are fabricated using similar components to earlier embodiments of fluid delivery devices disclosed in the present invention.

Cap 76 seals the top of container 72 and houses cell 74. Positioned below cap 76 is shield 78, which protects gas generating cell 74 from fluid 84 inside of container 72 inasmuch as shield 78 is air permeable, yet substantially moisture or water impermeable. Shield 78 is preferably fabricated from polypropylene. Elastomeric band seal 80 is positioned at the base of the container and can be laterally displaced by flanges 86 of container 72.

In operation, gas generating cell 74 is activated by a button or switch (not shown). Once activated, gas generating cell 74 continuously generates gas inside head space 88 of container 72, thereby building up pressure inside the container. The pressure in the container expands elastomeric band seals 80 allowing fluid to exit nib 82.

Alternatively, fluid dispensing device 70 can be operated without gas generating cell 74 in certain environments. For example, when there is rapid pressure change, such as, during take-off and assent in an airplane, the air in head space 88 rapidly expands and exerts pressure on elastomeric band seals 80 allowing fluid to dispense through the nib. The dispensed fluid can then evaporate throughout the duration of the flight. Upon descent the pressure will be normalized such that no fluid will be dispensed.

As shown in FIG. 8, fluid delivery device 70 will have cyclic fluid delivery characteristics at predetermined intervals depending on, among other things, whether the air plane is taking off, ascending, descending, or landing.

Turning now to FIG. 9, a fifth embodiment of fluid delivery device 100 is shown as comprising container 102, gas generating cell 104, aperture 106, emanator pad or fluid receiving surface 108, and fan 110. It will be understood that container 102 is preferably configured similar to container 32 of fluid dispensing device 30. It will be further understood that gas generating cell 104 is preferably configured similar to cell 34 of device 30.

For purposes of the present disclosure, aperture 106 is preferably positioned near the bottom of container 102 so that gravity may be used to assist gas generating cell 104 in dispensing fluid 114 from device 100. Although not shown, aperture 106 can be configured with a regulator such as a pin, a screw, or a cap to alter the size of the aperture. Emanator pad 108 is ideally positioned below the container and is preferably fabricated from, for example, polyurethane foam or nylon. It is also contemplated that the emanator be in direct contact with the aperture. It will likewise be understood that the emanator pad can be fabricated from any one of a number of materials so long as the material is substantially compatible with the fluid it temporarily retains. Indeed, emanator pad 108 can also be substituted with a material which holds fluid 114 onto its surface, such as glass or plastic.

In operation, gas generating cell 104 is activated by a button or switch (not shown), and can optionally be associated with shield 115—similar to shield 19 of FIG. 1. Once activated, gas generating cell 104 continuously generates gas inside container 102, thereby building up pressure inside of the container. With the assistance of gravity, the internal pressure forces fluid 114 inside of container 102 to exit through aperture 106 at a controlled rate. Once fluid 114 has exited container 102 it will deposit onto emanator pad 108. After fluid 114 is deposited onto emanator pad 108, it evaporates or volatilizes with the assistance of fan 110, which is preferably powered by battery 112 or other power sources. Once fluid 114 has evaporated, additional fluid will automatically be deposited onto the emanator pad. This cyclical process requires no mechanical manipulation beyond initially activating cell 104 and can run until either the cell is deactivated or expires, or the fluid is completely expelled from the container.

Although not shown, it will be understood that fluid delivery device 100 can be configured to operate without gas generating cell 104. In this configuration, cell 104 is replaced with a sealable aperture and gravity is solely responsible for dispensing the fluid onto the emanator pad 108.

In an alternative embodiment, fan 110 can be replaced, or used in conjunction with a gas generating cell 109, which would volatilize the fluid retained with the emanator pad. In such an embodiment, as the gas is generated, it permeates the emanator and assists in the volatilization of the fluid associated with the emanator.

FIG. 10 shows a schematic plot of delivery rate versus time for fluid delivery device 100. As can be seen from this plot, the delivery device exhibits relatively broad peaks which are indicative of a more continuous delivery into the atmosphere.

Turning now to FIG. 11, a sixth embodiment of fluid delivery device 120 is shown as comprising first container 122, gas generating cell 124, one-way valve 126, second container 128 and pressure relief valve 130. It will be understood that containers 122 and 128 and gas generating cell 124 are configured similar to container 12 and cell 18 of fluid dispensing device 10.

In operation, gas generating cell 124 is activated by a button or switch (not shown), and can be optionally associated with a shield 123—similar to shield 19 of FIG. 1. Once activated, gas generating cell 124 continuously generates gas inside container 122, thereby building up pressure inside the container. Once a threshold pressure is reached inside of the first container, one way valve 126 opens and allows a first fluid 132, such as water to enter into second container 128. The first fluid then contacts gas generating material 134, thereby causing a chemical reaction, with one of the products being a gas. It will be understood that any one of a number of gas generating materials are contemplated for use, the only limitation being that the material must be compatible with the container as well as the fluid that is to be dispensed from the container. The generated gas product increases pressure within second container 128 until a threshold pressure is reached and pressure relief valve 130 is opened allowing second fluid 136 to be expelled from the container. This process is cyclical (inasmuch as the pressure build up and controlled release of fluids from the first and second containers is a function of the pressure threshold of the associated valves) and will continue until either the cell or the associated fluid runs out.

It will be understood that each one of the aforementioned fluid delivery devices can dispense any one of a number of fluids including fragrances, perfumes, deodorizers, insect and/or bug repellants, medicants, to name a few.

The foregoing description and drawings merely explain and illustrate the invention and the invention is not limited thereto except insofar as the appended claims are so limited, as those skilled in the art who have the disclosure before them will be able to make modifications and variations therein without departing from the scope of the invention.

What is claimed is:

1. A fluid delivery device comprising:
    a container for holding a predetermined quantity of fluid;
    means for generating gas within the container; and
    means for cyclically dispensing fluid out of the container at predetermined intervals without cyclical actuation by a user.

2. The fluid delivery device according to claim 1, wherein the means for generating gas within the container comprises a gas generating cell.

3. The fluid delivery device according to claim 2, further comprising a shield to substantially preclude fluid within the container from contacting the gas generating cell.

4. The fluid delivery device according to claim 1, wherein the means for cyclically dispensing fluid comprises a one-way pressure relief valve.

5. The fluid delivery device according to claim 4, further comprising a stem for directing a fluid inside of the container toward the pressure relief valve.

6. The fluid delivery device according to claim 1, wherein the means for cyclically dispensing fluid comprises an aperture associated with the container.

7. The fluid delivery device according to claim 6, wherein the aperture is associated with a regulator to variably regulate the size of the aperture.

8. The fluid delivery device according to claim 6, further comprising a heater for vaporizing fluid.

9. The fluid delivery device according to claim 8, further comprising at least one of a battery, a solar powered cell, or a supply of alternating current.

10. The fluid delivery device according to claim 6, further comprising an emanator pad associated with the container.

11. The fluid delivery device according to claim 1, wherein the container is at least partially filled with at least one of the group consisting essentially of perfume, fragrance, deodorant fluids, insecticide fluids, sanitizing fluids, nutritional fluids, antimicrobial fluids, medication fluids and mixtures thereof.

12. A process for delivering fluid at predetermined intervals comprising the steps of:
    generating a gas within a container; and
    cyclically dispensing fluid out of the container with the generated gas without cyclical actuation by a user.

* * * * *